(12) United States Patent
Zaleski et al.

(10) Patent No.: US 9,287,102 B2
(45) Date of Patent: Mar. 15, 2016

(54) FAST-SWITCHING DUAL-POLARITY ION MOBILITY SPECTROMETRY

(75) Inventors: Henryk Zaleski, Mississaugua (CA); Mark Piniarski, Mississaugua (CA); Simon Feldberg, Mississaugua (CA); Jeff Anderson, Mississuagua (CA); Oleg Samarin, Toronto (CA)

(73) Assignee: SMITHS DETECTION MONTREAL INC., Laval (CA)

( * ) Notice: Subject to any disclaimer, the term of this patent is extended or adjusted under 35 U.S.C. 154(b) by 36 days.

(21) Appl. No.: 13/881,821

(22) PCT Filed: Oct. 27, 2011

(86) PCT No.: PCT/IB2011/002895
§ 371 (c)(1),
(2), (4) Date: Jul. 15, 2013

(87) PCT Pub. No.: WO2012/056322
PCT Pub. Date: May 3, 2012

(65) Prior Publication Data
US 2013/0284914 A1     Oct. 31, 2013

Related U.S. Application Data

(60) Provisional application No. 61/407,342, filed on Oct. 27, 2010, provisional application No. 61/407,327, filed on Oct. 27, 2010, provisional application No. 61/407,335, filed on Oct. 27, 2010.

(51) Int. Cl.
*G01N 27/62* (2006.01)
*H01J 49/04* (2006.01)
*G06K 9/00* (2006.01)
*H01J 49/02* (2006.01)
(Continued)

(52) U.S. Cl.
CPC ............... *H01J 49/04* (2013.01); *G01N 23/00* (2013.01); *G01N 27/622* (2013.01); *G06K 9/0053* (2013.01); *H01J 49/025* (2013.01); *H01J 49/06* (2013.01)

(58) Field of Classification Search
CPC ............................. G01N 27/622; H01J 49/025
See application file for complete search history.

(56) References Cited

U.S. PATENT DOCUMENTS 4,712,008 A * 12/1987 Vora et al. ..................... 250/287
4,855,595 A    8/1989 Blanchard et al.
(Continued)

OTHER PUBLICATIONS

International Search Report, International Patent Application No. PCT/IB2011/002895, mailed Apr. 10, 2012, 12 pages.
(Continued)

*Primary Examiner* — Jack Berman
*Assistant Examiner* — Kevin Chung
(74) *Attorney, Agent, or Firm* — Casimir Jones SC; David W. Staple

(57) ABSTRACT

Systems and methods disclosed provide for methods of managing polarity switching in an ion mobility spectrometer, and provide for management of the repelling grid voltage, the gating grid voltage, and the fixed grid voltage during polarity switching. Systems and methods also provide for the management of the effect of dielectric relaxation in an insulator proximal to the collector, and provide for a preamplifier coupled to the collector including a switch, and a method of managing the collector output including the switch. Systems and methods consistent with the current disclosure further provide for a method of normalizing ion mobility data by determining fitting coefficients associated with a plurality of measurement data sets, and subtracting the curves determined by the fitting coefficients from the data acquired by the ion mobility spectrometer.

7 Claims, 12 Drawing Sheets

(51) Int. Cl.
*H01J 49/06* (2006.01)
*G01N 23/00* (2006.01)

(56) References Cited

U.S. PATENT DOCUMENTS 5,200,614 A 4/1993 Jenkins et al.
5,796,099 A 8/1998 Jackson et al.
2003/0209665 A1* 11/2003 Losch et al. .................. 250/287

OTHER PUBLICATIONS

Zuleta et al., "Micromachined Bradbury-Nielsen Gates," Analytical Chemistry, 2007, 79(23): 9160-9165.

* cited by examiner

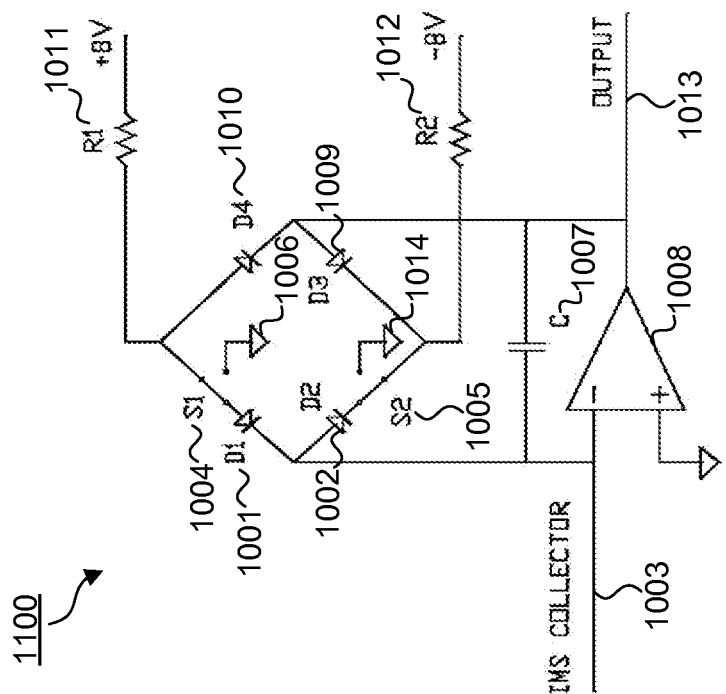
FIG. 11 SWITCH CLOSED
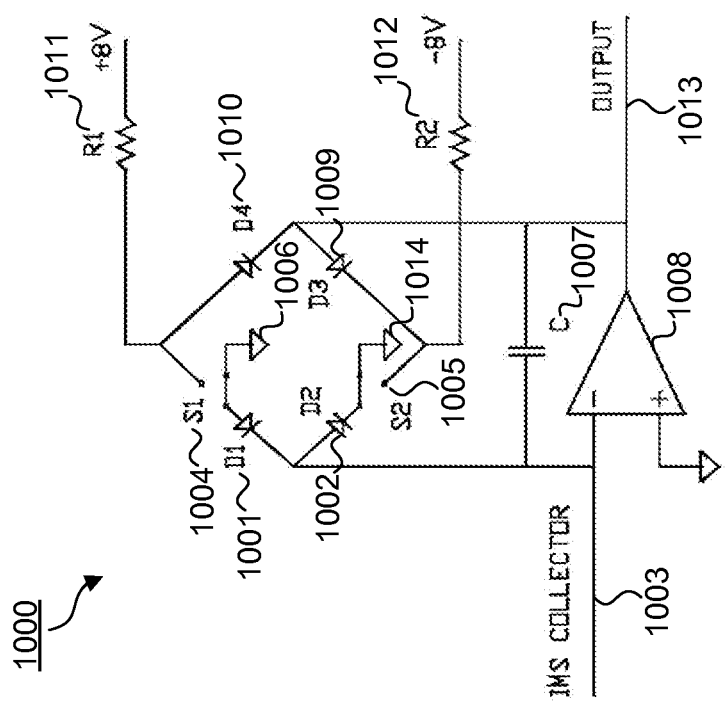
FIG. 10 SWITCH OPEN

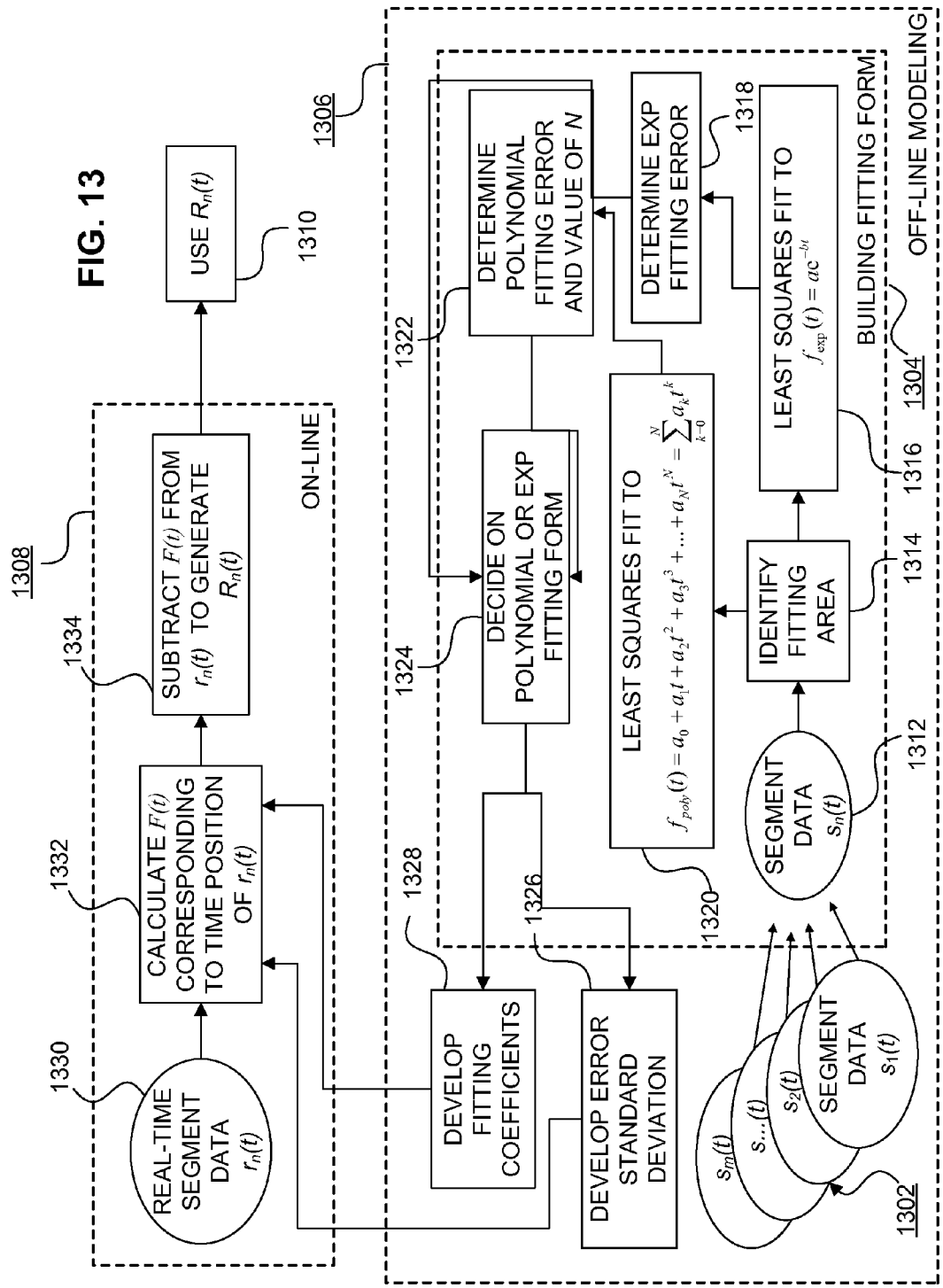

FAST-SWITCHING DUAL-POLARITY ION MOBILITY SPECTROMETRY

CROSS-REFERENCE TO RELATED APPLICATIONS

This application claims priority to U.S. Provisional Patent Application Ser. No. 61/407,327, filed Oct. 27, 2011, U.S. Provisional Patent Application Ser. No. 61/407,335, filed Oct. 27, 2011, and U.S. Provisional Patent Application Ser. No. 61/407,342, filed Oct. 27, 2011, each of which is incorporated by reference in its entirety.

FIELD OF THE INVENTION

This application is directed to dual-polarity ion mobility spectrometers.

BACKGROUND OF THE INVENTION

Ion mobility spectrometry is a method used to identify the composition of a sample of ions using ion mobility. Ion mobility spectrometers can be employed at security checkpoints, such as airports, to assist in the detection of explosives and narcotics. When used at airports, for example, residue from luggage can be transferred to a swab, which can be manipulated so that molecules and/or atoms associated with the residue pass into an ionization region within the ion mobility spectrometer. In the ionization region, the molecules and atoms associated with the residue can be ionized. Both positive and negative ions can form in the ionization region. An electric field at grids spaced between the ionization region and a drift region can be pulsed to allow ions to pass from the ionization region into the drift region. The ions in the drift region can be further subject to a force as a result of an electric field maintained in the drift region. Once in the drift region, the ions can separate based upon the ions' respective ion mobility. In this way, a time-of-flight measurement of the ions in the drift region (which can be measured as a change in current magnitude on a collector plate at one end of the drift region), can provide an identifying peak in a measured current magnitude, and which can be associated with a particular ion. The plot of current magnitude at the collector as a function of time is referred to as a plasmagram.

SUMMARY OF THE INVENTION

In one aspect, embodiments can provide a method of managing polarity switching, wherein the method can include operating an ion mobility spectrometer in a first mode. Consistent with the present disclosure, the first mode can be characterized by a first voltage of a repelling grid being more positive than a second voltage of a gating grid, and the second voltage of the gating grid being more positive than a third voltage of a fixed grid, and the third voltage of the fixed grid greater than zero, and wherein the ion mobility spectrometer can include the repelling grid, the gating grid, and the fixed grid. The method can further include operating the ion mobility spectrometer in a second mode, wherein the ion mobility spectrometer in the second mode can be characterized by the first voltage being more negative than the second voltage, and the second voltage being more negative than the third voltage, and the third voltage less than zero. The method can further include transitioning the first voltage in the first mode to the first voltage in the second mode, the second voltage in the first mode to the second voltage in the second mode, and the third voltage in the first mode to the third voltage in the second mode. Consistent with one aspect, during the transitioning step, the first voltage can be more positive than the second voltage when the second voltage is approximately equal to the third voltage, and the second voltage can be more negative than the first voltage when the first voltage is approximately equal to the third voltage. Consistent with a further aspect, the first voltage can be more positive than the second voltage during the transitioning of the second voltage in the first mode to the second voltage in the second mode, and during the transitioning of the third voltage in the first mode to the third voltage in the second mode.

In another aspect, embodiments can provide a further method of managing polarity switching, wherein the method can include operating an ion mobility spectrometer in a first mode. Consistent with the present disclosure, the first mode can be characterized by a first voltage of a repelling grid being more positive than a second voltage of a gating grid, and the second voltage of the gating grid being more positive than a third voltage of a fixed grid, and the third voltage of the fixed grid greater than zero, and wherein the ion mobility spectrometer can include the repelling grid, the gating grid, and the fixed grid. The method can further include operating the ion mobility spectrometer in a second mode, wherein the ion mobility spectrometer in the second mode can be characterized by the first voltage being more negative than the second voltage, and the second voltage being more negative than the third voltage, and the third voltage less than zero. The method can further include transitioning the first voltage in the second mode to the first voltage in the first mode, the second voltage in the second mode to the second voltage in the first mode, and the third voltage in the second mode to the third voltage in the first mode. During the transitioning step, the first voltage can be more negative than the second voltage when the second voltage is approximately equal to the third voltage, and the second voltage can be more positive than the first voltage when the first voltage is approximately equal to the third voltage. Consistent with a further aspect, the first voltage can be more negative than the second voltage during the transitioning of the second voltage in the second mode to the second voltage in the first mode, and during the transitioning of the third voltage in the second mode to the third voltage in the first mode.

In another aspect, embodiments can provide an ion mobility spectrometer. In this aspect, the ion mobility spectrometer can include a repelling grid configured to support a first voltage, a gating grid configured to support a second voltage, and a fixed grid configured to support a third voltage. The repelling grid, the gating grid, and the fixed grid can be configured to switch between operation according to positive ion mode with a closed gate and operation according to negative ion mode with a closed gate. In this aspect, operation in positive ion mode with a closed gate can be characterized by the first voltage being more positive than the second voltage, and the second voltage being more positive than the third voltage, and the third voltage being greater than zero. Furthermore, in this aspect, operation in negative ion mode with a closed gate can be characterized by the first voltage being more negative than the second voltage, and the second voltage being more negative than the third voltage, and the third voltage being less than zero. Further still, in this aspect, the ion mobility spectrometer can be configured to maintain the first voltage higher than the second voltage when the second voltage is approximately equal to the third voltage during a switch from positive ion mode with a closed gate to negative ion mode with a closed gate, and can be configured to maintain the first voltage lower than the second voltage when the second voltage is approximately equal to the third voltage during a switch from negative ion mode with a closed gate to positive ion mode with a closed gate.

In another aspect, embodiments can provide a computer-readable medium with instructions stored thereon, wherein the instructions cause one or more processors to perform a method of managing polarity switching. In this aspect, the method can include operating an ion mobility spectrometer in a first mode. The first mode can be characterized by a first voltage of a repelling grid being more positive than a second voltage of a gating grid, and the second voltage of the gating grid being more positive than a third voltage of a fixed grid, and the third voltage of the fixed grid greater than zero, and wherein the ion mobility spectrometer can include the repelling grid, the gating grid, and the fixed grid. The method can further include operating the ion mobility spectrometer in a second mode, wherein the ion mobility spectrometer in the second mode can be characterized by the first voltage being more negative than the second voltage, and the second voltage being more negative than the third voltage, and the third voltage less than zero. The method can further include transitioning the first voltage in the first mode to the first voltage in the second mode, the second voltage in the first mode to the second voltage in the second mode, and the third voltage in the first mode to the third voltage in the second mode. During the transitioning step, the first voltage can be more positive than the second voltage when the second voltage is approximately equal to the third voltage, and the second voltage can be more negative than the first voltage when the first voltage is approximately equal to the third voltage. Consistent with a further aspect, the first voltage can be more positive than the second voltage during the transitioning of the second voltage in the first mode to the second voltage in the second mode, and during the transitioning of the third voltage in the first mode to the third voltage in the second mode.

In another aspect, embodiments can provide a computer-readable medium with instructions stored thereon, wherein the instructions cause a processor to perform a further method of managing polarity switching. In this aspect, the method can include operating an ion mobility spectrometer in a first mode. The first mode can be characterized by a first voltage of a repelling grid being more positive than a second voltage of a gating grid, and the second voltage of the gating grid being more positive than a third voltage of a fixed grid, and the third voltage of the fixed grid greater than zero, and wherein the ion mobility spectrometer can include the repelling grid, the gating grid, and the fixed grid. The method can further include operating the ion mobility spectrometer in a second mode, wherein the ion mobility spectrometer in the second mode can be characterized by the first voltage being more negative than the second voltage, and the second voltage being more negative than the third voltage, and the third voltage less than zero. The method can further include transitioning the first voltage in the second mode to the first voltage in the first mode, the second voltage in the second mode to the second voltage in the first mode, and the third voltage in the second mode to the third voltage in the first mode. During the transitioning step, the first voltage can be more negative than the second voltage when the second voltage is approximately equal to the third voltage, and the second voltage can be more positive than the first voltage when the first voltage is approximately equal to the third voltage. Consistent with a further aspect, the first voltage can be more negative than the second voltage during the transitioning of the second voltage in the second mode to the second voltage in the first mode, and during the transitioning of the third voltage in the second mode to the third voltage in the first mode.

In an additional aspect, embodiments can provide an ion mobility spectrometer, wherein the ion mobility spectrometer can include a collector, an insulator, and a guard grid structure. In this aspect, the collector, the insulator, and the guard grid structure can be affixed together and proximal, and the collector can be in contact with the insulator and can be at a first potential. In this aspect, the guard grid structure can be configured to transition, at least once, between a second potential higher than the first potential and a third potential lower than the first potential, and the insulator and the guard grid structure can be configured such that a current acquired at the collector from a dielectric relaxation of the insulator in response to the transition is less than about 1 pA approximately 10 ms after a start of the transition from the second potential to the third potential, and while the guard grid structure is at the third potential.

In another aspect, embodiments can provide an ion mobility spectrometer that includes a collector, an insulator, and a guard grid structure, wherein the collector, the insulator, and the guard grid structure can be affixed together and proximal, and the collector can be in contact with the insulator and can be at a first potential. In this aspect, the guard grid structure can be configured to transition, at least once, between a second potential higher than the first potential and a third potential lower than the first potential, and the insulator and the guard grid structure can be configured such that a current acquired at the collector from a dielectric relaxation of the insulator in response to the transition is less than about 1 pA approximately 10 ms after a start of the transition from the third potential to the second potential, and while the guard grid structure is at the second potential.

In yet another aspect, embodiments can provide an ion mobility spectrometer that can include a collector, a guard grid structure, and a preamplifier. In this aspect, the preamplifier can be coupled to the collector and can include a first operational amplifier with an inverting input connected to the collector, a first capacitance connected between the inverting input and an output of the first operational amplifier, and a switch connected in parallel to the first capacitance. The collector can be at a first potential, and the guard grid structure can be configured to transition, at least once, between a second potential higher than the first potential and a third potential lower than the first potential. Further, the switch can be configured to be closed during the transition, and can be configured to be open after the guard grid structure at the third potential is substantially constant.

In a further aspect, embodiments can provide a method of managing collector output, wherein the method can include operating an ion mobility spectrometer in a first mode characterized by a guard grid structure at a second potential higher than a first potential, and operating the ion mobility spectrometer in a second mode characterized by the guard grid structure at a third potential lower than the first potential. The method can further include transitioning the guard grid structure at the second potential to the guard grid structure at the third potential, closing a switch during the transitioning step, and opening the switch after the transitioning step and after the third potential is substantially constant. In this aspect, the ion mobility spectrometer can include a collector, an insulator, the guard grid structure, and a preamplifier. The collector, the insulator, and the guard grid structure can be affixed together and proximal, and the collector can be in contact with the insulator and can be at the first potential. Consistent with the disclosure, the preamplifier can be coupled to the collector and can include a first operational amplifier with an inverting input connected to the collector, a first capacitor connected between the inverting input and an output of the first operational amplifier, and the switch connected in parallel to the first capacitor.

In a further aspect, embodiments can provide a computer-readable medium with instructions stored thereon, wherein the instructions cause one or more processors to perform a method of managing collector output. The method can include operating an ion mobility spectrometer in a first mode characterized by a guard grid structure at a second potential higher than a first potential, and operating the ion mobility spectrometer in a second mode characterized by the guard grid structure at a third potential lower than the first potential. The method can further include transitioning the guard grid structure at the second potential to the guard grid structure at the third potential, closing a switch during the transitioning step, and opening the switch after the transitioning step and after the third potential is substantially constant. In this aspect, the ion mobility spectrometer can include a collector, an insulator, the guard grid structure, and a preamplifier. The collector, the insulator, and the guard grid structure can be affixed together and proximal, and the collector can be in contact with the insulator and can be at the first potential. Consistent with the disclosure, the preamplifier can be coupled to the collector and can include a first operational amplifier with an inverting input connected to the collector, a first capacitance connected between the inverting input and an output of the first operational amplifier, and the switch connected in parallel to the first capacitance.

In another aspect, embodiments can provide a method of normalizing ion mobility data. The method can include developing a set of fitting coefficients from a plurality of time-dependent measurement sets and acquiring a set of drift time values comprising a plurality of drift time values. The at least one drift time value from the set of drift time values can have an associated collector value. The method can further include determining at least one collector contribution value associated with the at least one drift time value utilizing the set of fitting coefficients, and subtracting the at least one collector contribution value from the associated collector value to determine a normalized collector value. The plurality of time-dependent measurement sets can include at least one time-dependent measurement set generated by an ion mobility spectrometer. Further, the at least one time-dependent measurement set can include a first plurality of time-dependent measurements, wherein each time-dependent measurement in the first plurality of time-dependent measurements has an associated error range, and wherein the at least one time-dependent measurement set and associated set of error ranges can be consistent with a time-dependent curve. The step of developing a set of fitting coefficients from a plurality of time-dependent measurement sets can include fitting the at least first plurality of time-dependent measurements to one function of the set of: a polynomial function of time and an exponential function of time.

In another aspect, embodiments can provide a further method of normalizing ion mobility data. The method can include acquiring a set of drift time values comprising a plurality of drift time values, wherein at least one drift time value from the set of drift time values has an associated collector value. The method can further include determining at least one collector contribution value associated with the at least one drift time value utilizing a set of fitting coefficients, and subtracting the at least one collector contribution value from the associated collector value to determine a normalized collector value. The set of fitting coefficients can be developed from at least one time-dependent measurement set generated by an ion mobility spectrometer, wherein the time-dependent measurement set can be fitted to one function of the set of: a polynomial function of time and an exponential function of time. The at least one time-dependent measurement set can include a first plurality of time-dependent measurements. Further, the time-dependent measurements can have an associated error range, wherein the at least one time-dependent measurement set and associated set of error ranges can be consistent with a time-dependent curve.

In another aspect, embodiments can provide a computer-readable medium with instructions stored thereon, wherein the instructions cause a processor to perform a method of normalizing ion mobility data. The method can include developing a set of fitting coefficients from a plurality of time-dependent measurement sets and acquiring a set of drift time values comprising a plurality of drift time values. Consistent with the current disclosure the at least one drift time value from the set of drift time values can have an associated collector value. The method can further include determining at least one collector contribution value associated with the at least one drift time value utilizing the set of fitting coefficients, and subtracting the at least one collector contribution value from the associated collector value to determine a normalized collector value. The plurality of time-dependent measurement sets can include at least one time-dependent measurement set generated by an ion mobility spectrometer. Further, the at least one time-dependent measurement set can include a first plurality of time-dependent measurements, wherein each time-dependent measurement in the first plurality of time-dependent measurements has an associated error range, and wherein the at least one time-dependent measurement set and associated set of error ranges can be consistent with a time-dependent curve. Further, the step of developing a set of fitting coefficients from a plurality of time-dependent measurement sets can include fitting the at least first plurality of time-dependent measurements to one function of the set of: a polynomial function of time and an exponential function of time.

Further still, in another aspect, embodiments can provide a computer-readable medium with instructions stored thereon, wherein the instructions cause a processor to perform a further method of normalizing ion mobility data. In this aspect, the method can include acquiring a set of drift time values comprising a plurality of drift time values, wherein at least one drift time value from the set of drift time values has an associated collector value. The method can further include determining at least one collector contribution value associated with the at least one drift time value utilizing a set of fitting coefficients, and subtracting the at least one collector contribution value from the associated collector value to determine a normalized collector value. The set of fitting coefficients can be developed from at least one time-dependent measurement set generated by an ion mobility spectrometer, wherein the time-dependent measurement set can be fitted to one function of the set of: a polynomial function of time and an exponential function of time. The at least one time-dependent measurement set can include a first plurality of time-dependent measurements. Further, the time-dependent measurements can have an associated error range, wherein the at least one time-dependent measurement set and associated set of error ranges can be consistent with a time-dependent curve.

Additional features and embodiments of the invention will be set forth in part in the description which follows, and in part will be obvious from the description, or may be learned by practice of the invention. It is to be understood that both the foregoing general description and the following detailed description are exemplary and explanatory only and are not restrictive of the claimed subject matter.

BRIEF DESCRIPTION OF THE DRAWINGS

The accompanying drawings, which are incorporated in and constitute a part of this specification, illustrate exemplary embodiments and together with the description, serve to explain the principles of the disclosure.

FIGS. 10 and 11 depict a switch consistent with an embodiment of the circuit of FIG. 8.

FIG. 13 schematically depicts steps associated with the normalization of the plasmagram of FIG. 12 consistent with an embodiment.

DETAILED DESCRIPTION OF THE INVENTION

Reference will now be made in detail to the disclosed embodiments of the disclosure, examples of which are illustrated in the accompanying drawings. Wherever possible, the same reference numbers will be used throughout the drawings to refer to the same or like parts.

Figure 3:
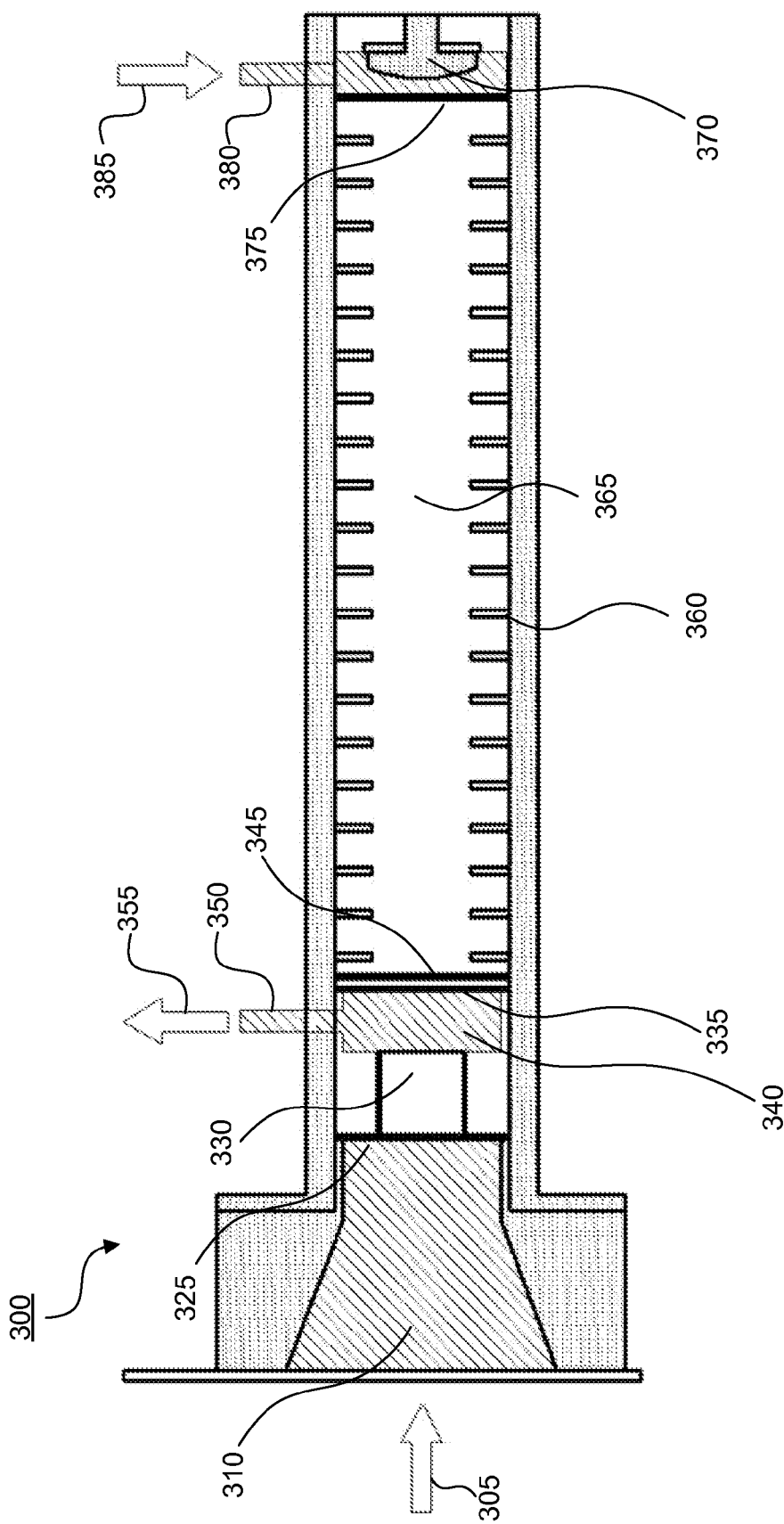
FIG. 3 is a cross-sectional view of an ionization region and a drift region of an ion mobility spectrometer consistent with an embodiment.

A portion of an ion mobility spectrometer 300 consistent with an embodiment is depicted in FIG. 3. Molecules and/or atoms associated with a sample being tested can enter through an inlet 310 (depicted with arrow 305). Sample molecules and/or atoms then pass a repelling grid 325 into an ionization region 340. The repelling grid 325 can comprise inert metal (e.g., gold-plated nickel), and can have a grid spacing of about 0.1 mm. The ionization region 340 can include a region with an ionization source 330. The ionization source 330 can comprise a material, such as Nickel-63. Alternatively, ions can be created in ionization region 340 as a result of corona discharge ionization, photoionization, electrospray ionization, matrix assisted laser desorption ionization (MALDI), or the like.

The ion mobility spectrometer 300 can operate in positive ion mode and negative ion mode. In these modes, certain components of the ion mobility spectrometer 300 can exhibit voltages in order to create an electric field along the length of the ion mobility spectrometer 300. When the ion mobility spectrometer 300 is operating in positive ion mode, for example, the repelling grid 325 can exhibit a relatively high positive voltage. As described further below, when operating in positive ion mode, other components of ion mobility spectrometer 300 located towards the opposite end of the ionization region 340 and across the drift region 360 will exhibit lower voltages. This configuration will create an electric field in the ionization region 340, for example, that directs positive ions away from the inlet 310. In an embodiment, the magnitude of the positive voltage on the repelling grid 325 can be about 2100 V. The range of magnitudes of the positive voltage on the repelling grid 325 can be 1000V to 5000V. Example values can be higher or lower depending upon the physical dimensions of the system. Both a fixed grid 335 and a gating grid 345 are located between the ionization region 340 and the drift region 365. As discussed above, and in positive ion mode, the fixed grid 335 can exhibit a voltage that is less than the positive voltage on the repelling grid 325 such that there is a potential gradient (i.e., an electric field) oriented across the ionization region 340. Other components can also be present between the repelling grid 325 and the fixed grid 335 in the ionization region 340 in support of an electric field in the ionization region 340. In an embodiment, when the voltage on the repelling grid 325 is approximately 2100 V as described above, the fixed grid 335 can exhibit a positive voltage that is approximately 1810 V. The voltage on the fixed grid 335 can be chosen so the potential gradient near the fixed grid 335 in the ionization region 340 and near the fixed grid 335 in the drift region 365 will provide a force on ions that will direct the ions from the ionization region 340 to the drift region 365 when the gating grid 345 is "open" (as is described further below). By way of example only, and without limitation, a configuration that allows for a uniform electric field across the barrier between the ionization region 340 and the drift region 365 is a configuration that can provide a substantially uniform force on an ion to direct ions (of one polarity) from the ionization region 340 to the drift region 365. According to the above embodiment, an electric field across the ionization region 340 can have a magnitude that ranges from 50 V/cm to 500 V/cm. The electric field in the ionization region does not need to be uniform throughout the ionization region 340. However, the electric field in the drift region 365 can be generally uniform. For example, where the drift region 365 is approximately 6.9 cm, and the electric field across the drift region 365 also has a magnitude of approximately 250 V/cm, the voltage on a guard grid 375 at one end of drift region 365 can be approximately 90 V. In other embodiments, the range of values for an electric field in the drift region 365 can be 200 V/cm to 300 V/cm.

Adjacent to the fixed grid 335 is the gating grid 345, where the gating grid 345 can be positioned so the fixed grid 335 is between the repelling grid 325 and the gating grid 345. The gating grid 345 can be approximately 0.75 mm from the fixed grid 335. A shutter structure consistent with the combination of the fixed grid 335 and the gating grid 345 is referred to as a Bradbury-Nielsen gate. Other suitable gates include, but are not limited to, Tyndall's gate. The combination of the fixed grid 335 and the gating grid 345 can comprise two sets of parallel wires (which can be two etched foils), where the spacing between the wires of the respective grids can be about 0.8 mm. The parallel wires on the grids can be oriented in the same direction, but can be spaced so, when viewed from a direction that is perpendicular to the plane of the grid, the wires are interleaved. There can also be an insulating foil of thickness about 0.75 mm between the grids. The fixed grid 335 and gating grid 345 can comprise Invar or other materials. In positive ion mode, the gating grid 345 can be kept at a higher voltage than the fixed grid 335 to create a barrier along the potential gradient between the ionization region 340 and the drift region 365. When the gating grid 345 is at a higher potential than the fixed grid 335, the gating grid 345 is referred to as "closed." The difference in voltage between the gating grid 345 and the fixed grid 335, when the gating grid 345 is closed, can be about 20 V. The voltage of the gating grid 345 can have a magnitude of about 1830 V in positive ion mode. Such a magnitude can have the effect of introducing an electric field that interferes with the passage of positive ions from the ionization region 340 through the drift region 365 to a collector 370 (described further below).

After molecules and/or atoms have entered the ionization region 340 and positive ions form, the repelling grid 325 can be maintained at a high voltage, as described above, and the gating grid 345 can remain closed for approximately 20 milliseconds. After this time period elapses, a negative voltage pulse can be applied to the gating grid 345 to open the gating grid 345 and allow positive ions to move from the ionization region 340 to the drift region 365 so the positive ions may travel toward the collector 370. In an embodiment, when the gating grid 345 is approximately 20 V higher than the fixed grid 335 when closed, the negative voltage pulse to the gating grid 345 can have an amplitude of approximately 25 V to open the gating grid 345. In an embodiment, the negative voltage pulse applied to the gating grid 345 to open the gating grid 345 can have an amplitude so the potential gradient at the boundary between the ionization region 340 and the drift region 365 directs positive ions from the ionization region 340 to the drift region 365 so positive ions can arrive at the collector 370. A time period permitted for the ions to move from the ionization region 340 to the drift region 365 (when the gating grid 345 is open) can be about 200 microseconds. The gating grid 345 can be open for about 200-300 microseconds, but can be open for as short as about 50 microseconds and open for as long as about 1000 microseconds. Opening the shutter structure (such as by pulsing the voltage on the gating grid 345) for this duration, and then closing the shutter structure can allow positive ions to move into the drift region 365 so the positive ions can arrive at the collector 370. In the drift region, an electric field can provide a force on the positive ions to direct the positive ions through the drift region 365 towards the guard grid 375 and the collector 370. The collector 370 can be any suitable structure for detecting pulses of current associated with moving ions, such as a Faraday plate. As the positive ions move through the drift region 365 towards the collector 370, the positive ions can move through a drift gas. In an embodiment, the drift gas can move in the opposite direction to the flow of the positive ions, where the flow of positive ions is towards the collector 370. The drift gas can enter the drift region 365 from a drift flow 380 (indicated by arrow 385) and exit the ion mobility spectrometer 300 through an exhaust flow 350 (indicated by arrow 355). The drift gas in the drift region 365 can be dry air, although other gases such as nitrogen or helium can be used. As the ions move through the drift region 365 toward the collector 370, various species of ions can separate as a function of their mobility. The drift time of the ions across the drift region 365 can vary depending on their atomic and/or molecular characteristics and the temperature and pressure of the drift gas. For a drift region 365 that is approximately 6.9 cm in length and at normal atmospheric pressure and temperature, the drift time can be in the range of 5 milliseconds to 20 milliseconds. Furthermore, the time period during which data is acquired from the collector 370 associated with one scan can range from about 2 milliseconds to about 40 milliseconds. In an embodiment, one scan can represent a 25 millisecond time period.

Accordingly, electric current values can be measured at regular time intervals at the collector 370, corresponding to time-of-flight signatures of the ionic species that can make up the positive ions present in the drift region 365. As discussed above, in an embodiment, the drift gas can flow in the opposite direction from the movement of the positive ions being measured at the collector 370 in positive ion mode. Such a drift gas flow can be used to keep the drift gas pure, but a flow is not required for operation of the ion mobility spectrometer 300. Other methods and systems for maintaining drift gas purity can include placing sorbent material within the drift region 365.

In an embodiment, as described above, the voltage difference between the gating grid 345 and the guard grid 375 can be approximately 1720 V and the distance between the gating grid 345 and the guard grid 375 can be 6.9 cm. The magnitude of the voltage of the guard grid 375 can be approximately 90 V.

Drift rings 360 can be employed in drift region 365. In an embodiment, the drift rings 360 can be flat metal rings, spaced at regular intervals between the gating grid 345 and the guard grid 375 and can be biased at equal voltage steps to improve uniformity of the potential gradient (that is, the uniformity of the electric field) within the drift region 365.

Operation of the ion mobility spectrometer 300 in negative ion mode is similar, in principle, to its operation in positive ion mode. The relative voltages on the repelling grid 325, the fixed grid 335, the gating grid 345, and the guard grid 375, however, are inverted. Specifically, the repelling grid 325 can be more negative than the fixed grid 335, which can be more negative than the guard grid 375. In an embodiment of the ion mobility spectrometer 300 operating in negative ion mode, the magnitude of the voltages associated with the repelling grid 325, the fixed grid 335, the gating grid 345, and the guard grid 375 can be approximately similar in magnitude but with opposite polarity to those recited above in positive mode. Specifically, the repelling grid 325 can be approximately −2100 V, the fixed grid 335 can be approximately −1810 V, the guard grid 375 can be approximately −90 V, and the gating grid 345 can be approximately −1830 V when closed, and pulsed to approximately −1805 V when open. The voltage across the drift rings 360 can also be inverted from the circumstance described in positive ion mode to form a uniform potential gradient through the drift region 360. In this way, the potential gradient in negative ion mode is inverted from the potential gradient described above in connection with positive ion mode thereby inverting the direction of the electric field across the ionization region 340 and the drift region 365 of the ion mobility spectrometer 300.

As described above, the drift region 365 can have an electric field applied along its length, and the slope of the potential field as a function of distance (i.e., the direction of the electric field associated with the potential gradient) can be positive or negative depending on the charge of the ions. Ions of a similar polarity can move from the ionization region 340 into the drift region 365 by the opening and closing of the gating grid 345. The time period of a scan of a collection of ions in the drift region 365 is the time period between when the gating grid 345 opens to admit ions into the drift region 365 from the ionization region 340, and the subsequent opening of the gating grid 345 to admit additional ions into the drift region 365 from the ionization region 340. The interval between subsequent voltage pulses applied to gating grid 345 so that it opens (e.g., negative voltage pulses for operation in positive ion mode and positive voltage pulses for operation in negative ion mode) is referred to as the "scan period." Current measurements that are acquired from the collector 370 from several subsequent scans can be co-added together to improve signal-to-noise of the mobility spectrum reflected in the scans. This collection of data may be referred to as a "segment." Data associated with one segment can be acquired in less than a second (e.g., data associated with one segment can be acquired by co-adding approximately 40 scans or less, where the scans have a duration of approximately 25 milliseconds). A series of sequential segments, with characteristic ion peak patterns, can be obtained and can be displayed either as a series of individual segments versus desorption time in seconds (a three-dimensional plasmagram) or as an average of all segments obtained during the analysis (a two-dimensional plasmagram). The desorption time is the time associated with the desorption of molecules and atoms from the swab, such as through the application of heat. The desorption of the molecules and atoms from the swab through the application of heat, for example, can make the molecules and atoms available to pass through the inlet 310 and into the ionization region 340.

As described above, in positive ion mode, the gating grid 345 can be kept at a higher voltage than the fixed grid 335 to create a barrier along the potential gradient between the ionization region 340 and the drift region 365. When the gating grid 345 is at a higher potential than the fixed grid 335, the gating grid 345 is referred to as "closed." Further, as described above, the difference in voltage between the gating grid 345 and the fixed grid 335, when the gating grid 345 is closed, can be about 20 V. Such a magnitude can have the effect of supporting an electric field that interferes with the passage of positive ions from the ionization region 340 through the drift region 365 to the collector 370. Moreover, a negative voltage pulse can be applied to the gating grid 345 to open the gating grid 345 and allow positive ions to move from the ionization region 340 to the drift region 365 so the positive ions may travel toward the collector 370. In an embodiment, when the gating grid 345 is approximately 20 V higher than the fixed grid 335 when closed, the negative voltage pulse to the gating grid 345 can have an amplitude of approximately 25 V to open the gating grid 345. In a further embodiment, a positive voltage pulse of approximately 25 V can be applied to the fixed grid 335, while the gating grid 345 is left unchanged in order to "open" the shutter structure associated with the combination of the fixed grid 335 and the gating grid 345 in positive ion mode. That is, in a further embodiment, and rather than applying a negative voltage pulse to the gating grid 345 while the fixed grid 335 is left unchanged, a positive voltage pulse can be applied to the fixed grid 335 while the gating grid 345 is left unchanged. Further still, in further embodiments, a positive voltage pulse of approximately N volts can be applied to the fixed grid 335 and a negative voltage pulse of approximately 25−N volts can be applied to the gating grid 345 in order to "open" the shutter structure associated with the combination of the fixed grid 335 and the gating grid 345 in positive ion mode.

Further still, and as described above, in negative ion mode, the gating grid 345 can be kept at a lower voltage than the fixed grid 335 to create a barrier along the potential gradient between the ionization region 340 and the drift region 365. When the gating grid 345 is at a lower potential than the fixed grid 335, the gating grid 345 is referred to as "closed." Further, as described above, the difference in voltage between the gating grid 345 and the fixed grid 335, when the gating grid 345 is closed, can be about 20 V. Again, such a magnitude can have the effect of supporting an electric field that interferes with the passage of negative ions from the ionization region 340 through the drift region 365 to the collector 370. Further still, a positive voltage pulse can be applied to the gating grid 345 to open the gating grid 345 and allow negative ions to move from the ionization region 340 to the drift region 365 so the negative ions may travel toward the collector 370. In an embodiment, when the gating grid 345 is approximately 20 V lower than the fixed grid 335 when closed, the positive voltage pulse to the gating grid 345 can have an amplitude of approximately 25 V to open the gating grid 345. In a further embodiment, a negative voltage pulse of approximately 25 V can be applied to the fixed grid 335, while the gating grid 345 is left unchanged in order to "open" the shutter structure associated with the combination of the fixed grid 335 and the gating grid 345 in negative ion mode. That is, in a further embodiment, and rather than applying a positive voltage pulse to the gating grid 345 while the fixed grid 335 is left unchanged, a negative voltage pulse can be applied to the fixed grid 335 while the gating grid 345 is left unchanged. Further still, in further embodiments, a negative voltage pulse of approximately N volts can be applied to the fixed grid 335 and a positive voltage pulse of approximately 25−N volts can be applied to the gating grid 345 in order to "open" the shutter structure associated with the combination of the fixed grid 335 and the gating grid 345 in negative ion mode.

Figure 4:
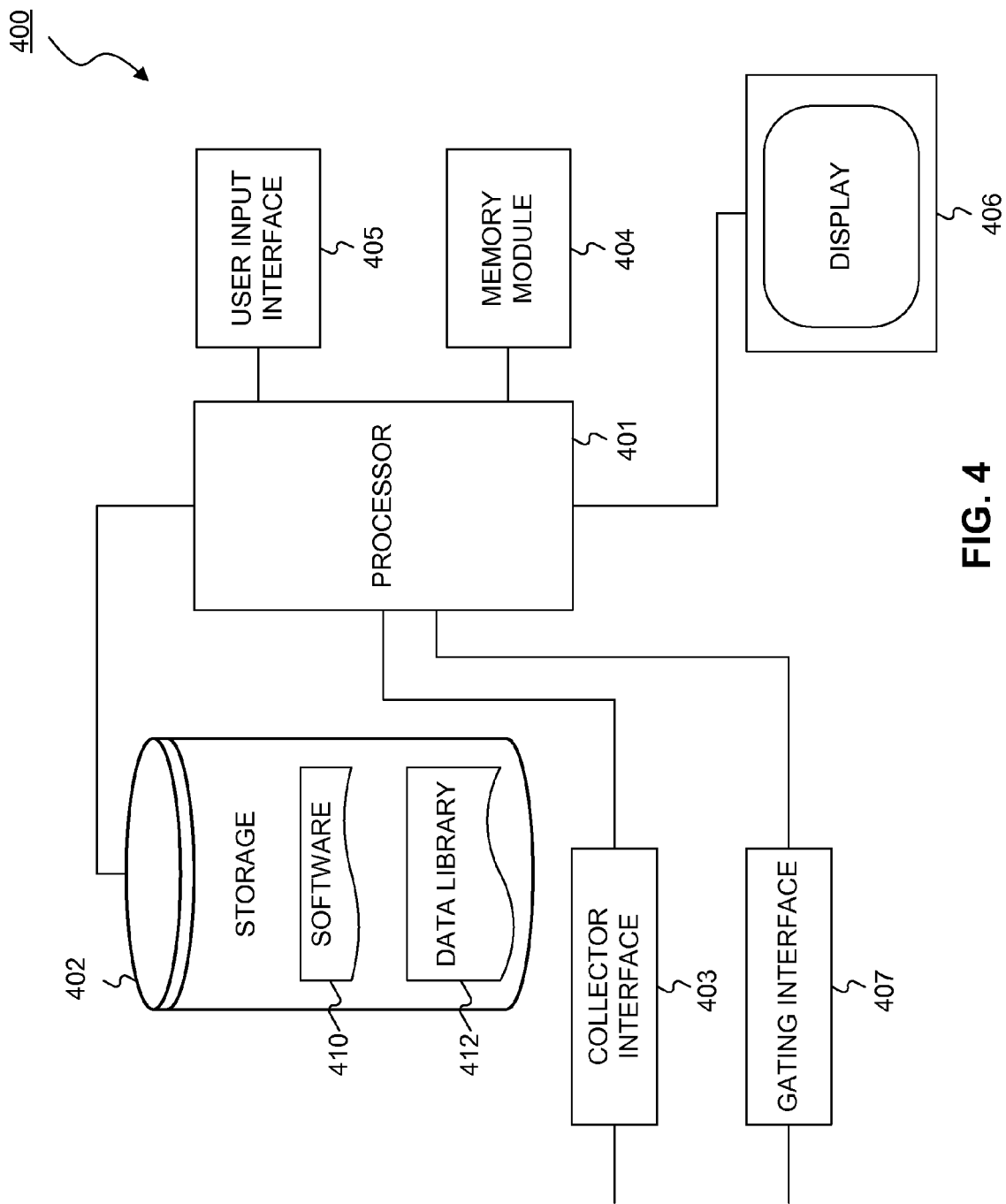
FIG. 4 depicts an data processing system consistent with an embodiment.

Consistent with an embodiment, the ion mobility spectrometer 300 includes a data processing system 400. FIG. 4 is a schematic diagram of the data processing system 400. The data processing system 400 can include a processor 401, a memory module 404, a collector interface 403, a storage 402, a user input interface 405, a display 406, a gating interface 407, and a mode polarity manager 408. The data processing system 400 can include additional, fewer, and/or different components than those listed above. The type and number of listed devices are exemplary only and not intended to be limiting.

The processor 401 can be a central processing unit ("CPU") included in a computing device, such as a computer configured to execute a program of instructions. The processor 401 can execute sequences of computer program instructions to perform various processes that are described throughout this document. The memory module 404 can include, among other things, a random access memory ("RAM") and a read-only memory ("ROM"). The computer program instructions can be accessed and read from the ROM, the storage 402 (such as a software 410), or any other suitable memory location, and loaded into the RAM for execution by the processor 401. Although the software is depicted as being stored on storage 402, e.g., a hard drive, the instructions comprising the software may be stored in a wide variety of tangible storage media. It is the intention of this disclosure to encompass such variations. Depending on the type of data processing system 400 being used, the processor 401 can include one or more processors included on printed circuit boards, and/or microprocessor chips.

Collector interface 403 can be configured to receive signals from the collector 370 such that processor 401, for example, may store data representing the signals output by the collector in the storage 402.

The storage 402 can include any type of storage suitable for storing information. For example, the storage 402 can include one or more hard disk devices, optical disk devices, or any other storage devices that can retain the data. In an embodiment, the storage 402 can store data related to the data processing process, such as the scan data received from the collector 370, and any intermediate data created during the data processing process. The storage 402 can also include analysis and organization tools for analyzing and organizing the information contained therein, such as a data library 412 that can include data associated with plasmagram peak positions, peak amplitudes, peak widths, and/or reduced ion mobility values. In addition, the gating interface 407, via the hardware included in the data processing system can be configured to provide a signal, such as a pulse, to open the gating grid 345.

A user may implement the user input interface 405 to input information into the data processing system 400, and can include, for example, a keyboard, a mouse, a touch screen, and/or optical or wireless computer input devices (not shown). The user can input control instructions via the user input interface 405 to control the operation of the ion mobility spectrometer 300. For example, the user can input parameters to adjust the operation of the data processing system 400 and or the ion mobility spectrometer 300.

The mode polarity manager 408 can be configured to manage the various voltages associated with components of the ion mobility spectrometer 300, such as the repelling grid 325, the fixed grid 335, the gating grid 345 (in closed mode, for example), the drift rings 360, and the guard grid 375. The mode polarity manager 408 can be configured to control when and in what order the various components change polarities as the ion mobility spectrometer 300 changes modes.

One or more modules of the data processing system 400 can be used to determine characteristics of plasmagram peaks and whether the characteristics are within predetermined and/or derived ranges. The data processing system 400 can be used to normalize a plasmagram and/or data associated with the plasmagram. The storage 402 can also store a detection library (such as in the data library 412), which can include characteristics of plasmagram peaks of known materials and/or other data, such as reduced ion mobility values. The storage 412 can also store timing information relating to switching frequencies or clear-down periods, and so forth.

Figure 5:
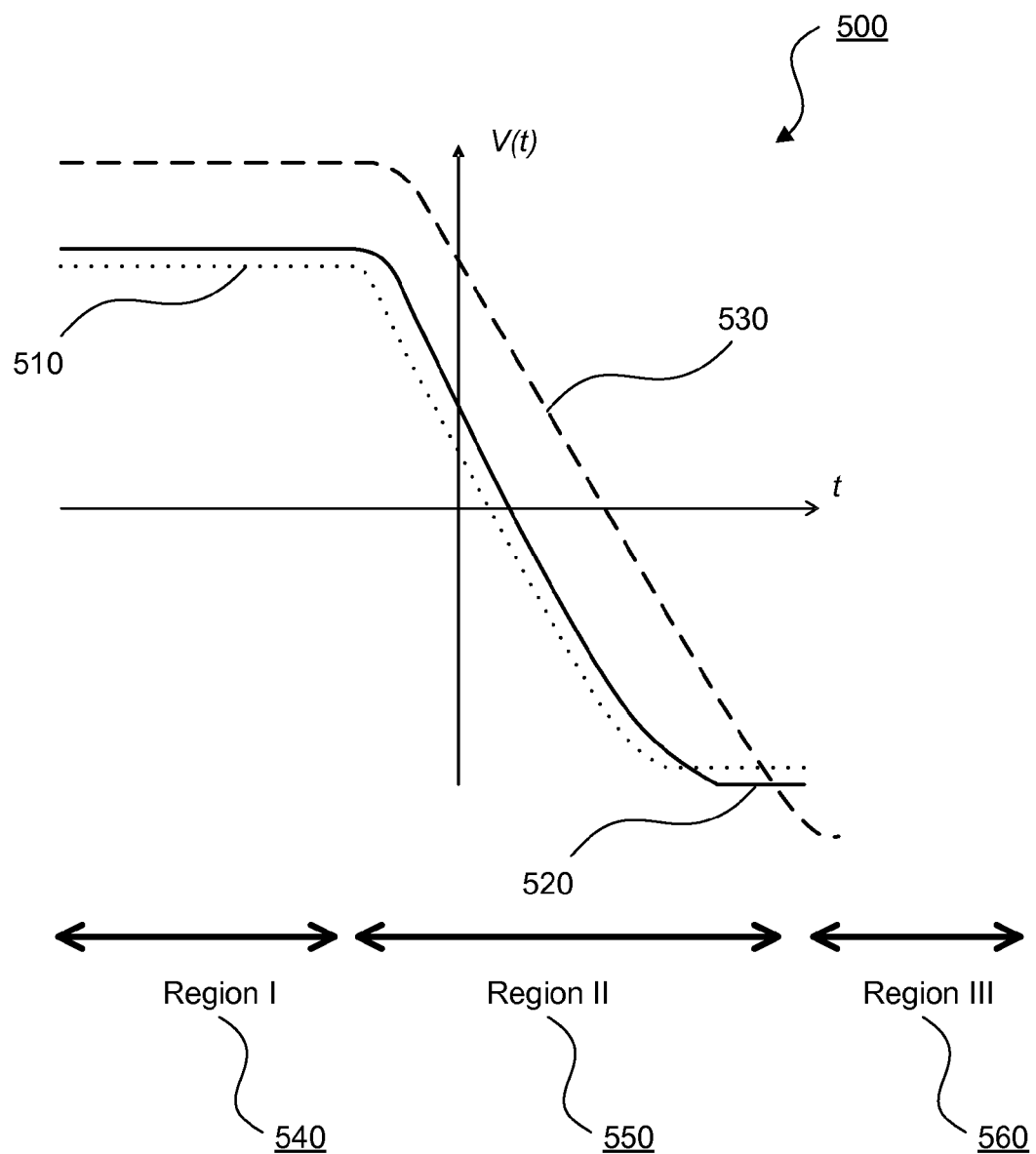
FIG. 5 depicts example voltages as a function of time on a repelling grid, a gating grid, and a fixed grid of an ion mobility spectrometer during a change from positive ion mode to negative ion mode.

FIG. 5 is a plot of exemplary voltages on the repelling grid 325 (dashed curve 530), the gating grid 345 (curve 520), and the fixed grid 335 (dotted curve 510), such as the ion mobility spectrometer 300 operating during a transition from positive ion mode (Region I 540) to negative ion mode (Region III 560). In Region I 540 (positive ion mode), the voltage on the repelling grid 325 (the dashed curve 530) is more positive than the voltage on the gating grid 345 (the solid curve 520), which is more positive than the voltage on the fixed grid 335 (dotted curve 510). These relative voltage magnitudes can correspond to a gating grid 345 that is closed in positive ion mode. In Region III 560 (negative ion mode), the voltage on the repelling grid 325 (dashed curve 530) is more negative than the voltage on the gating grid 345 (curve 520), which is more negative than the voltage on the fixed grid 335 (dotted curve 510). These relative voltage magnitudes can correspond to a gating grid 345 that is closed in negative ion mode. Between the two regions, Region I 540 and Region III 560, and before dotted curve 510 (which corresponds to the voltage on the fixed grid 335) crosses solid curve 520 (which corresponds to the voltage on the gating grid 345), dashed curve 530 (which corresponds to the voltage on the repelling grid 325) is kept at a higher potential than both solid curve 520 and dotted curve 510—indicating that the voltage on the repelling grid 325 will continue to be more positive than the voltage on both of the gating grid 345 and the fixed grid 335. Accordingly, during polarity switchover in Region II 550, when there can be negative ions present in the ionization region 340, and where the relative voltages between the gating grid 345 and the fixed grid 335 correspond to an open gate in negative ion mode, the repelling grid 325 (the dashed curve 530) is kept high relative to the fixed grid 335 (dotted line 510) and the gating grid 345 (solid curve 520). The relative voltage depicted in FIG. 5 between the repelling grid 325 and the gating grid 345 can keep the negative ions away from the gating grid 345 (and thereby the drift region 365) until after the dotted curve 510 crosses the solid curve 520. When dotted curve 510 crosses solid curve 520 and the relative voltage of the gating grid 345 is less than the voltage of the fixed grid 335, the gating grid 345 is closed in negative ion mode. After that occurs, and the gating grid 345 is closed, the magnitude of the voltage on the repelling grid 325 can pass below both the voltage of the gating grid 345 and the voltage of the fixed grid 335, thereby repelling the negative ions in the ionization region 340 towards the fixed grid 335 and the gating grid 345. In an embodiment, the time that the ion mobility spectrometer 300 spends in Region II 550 can be approximately 2 milliseconds.

Figure 6:
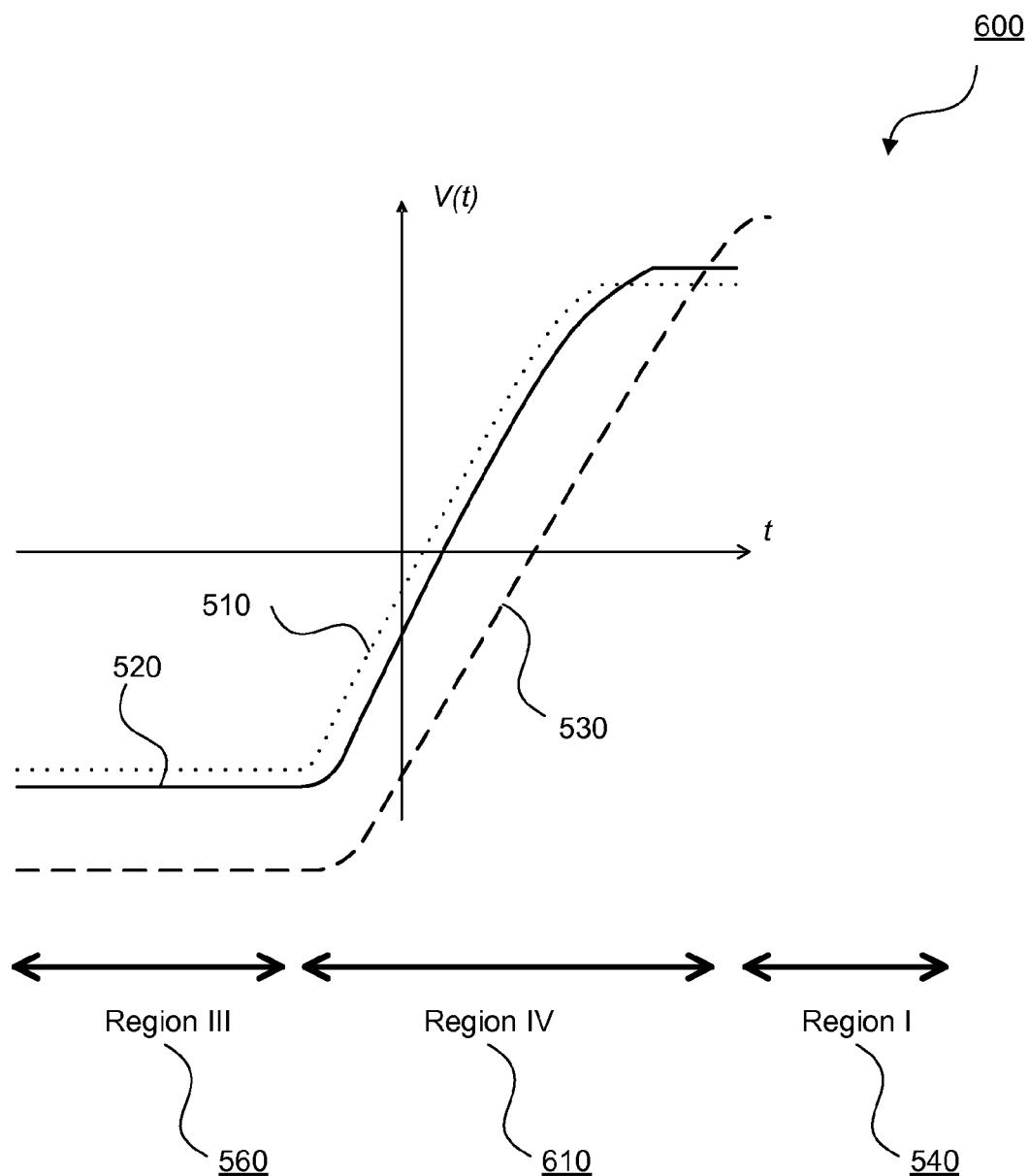
FIG. 6 depicts example voltages as a function of time on a repelling grid, a gating grid, and a fixed grid of an ion mobility spectrometer during a change from negative ion mode to positive ion mode.

FIG. 6 depicts the similar sequence of inverted crossings that can be used consistent with the current disclosure to pass from operation in negative ion mode (Region III 560) with a closed gating grid 345 to operation in positive ion mode (Region I 540) with a closed gating grid 345. Again, the voltage on the repelling grid 325 (the dashed curve 530) can be kept low relative to the voltage of both the gating grid 345 (curve 520) and the fixed grid 335 (dotted curve 510) until the voltage of the gating grid 345 crosses over and becomes greater than the voltage on the fixed grid 335. At that point, as has been described, the gating grid 345 has become closed in positive ion mode, and then the repelling grid 325 (dashed curve 530) can cross both the voltage of the fixed grid 335 and the voltage of the gating grid 345 and create a potential gradient in the ionization region 340 that drives the positive ions towards the gating grid 345. In an embodiment, the time that the ion mobility spectrometer 300 spends in Region IV 610 can be approximately 2 milliseconds.

During intervals when sample molecules are not being introduced into ionization region 140, known as idle operation, a system, consistent with the present embodiment, can suppress polarity switching. Such suppression can help to minimize the production of ionic species that can compete for charge with the ions of interest (including explosives and narcotics).

Figure 1:
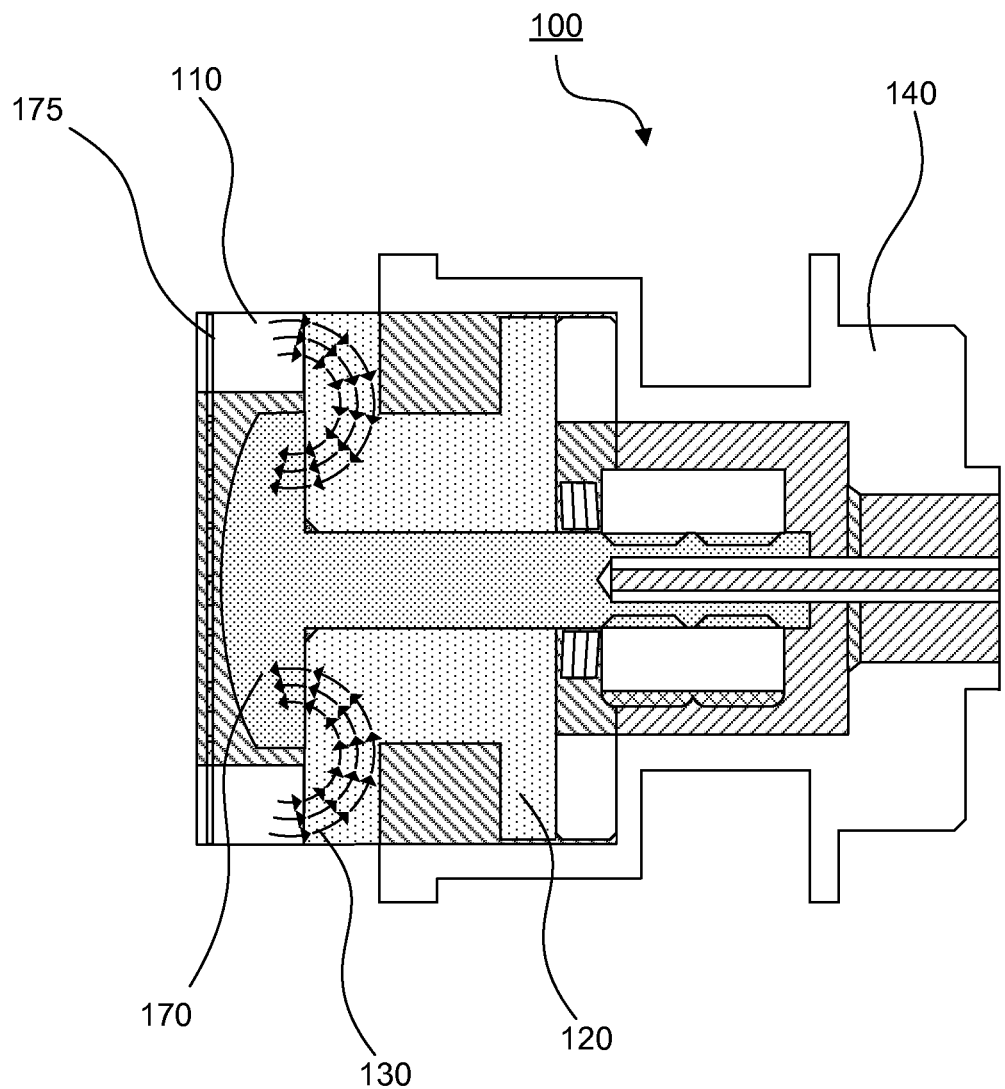
FIG. 1 is a cross sectional view of a portion of an ion mobility spectrometer.

By way of example only, FIG. 1 depicts a cross section of a portion of an ion mobility spectrometer 100 showing a collector 170, a guard grid 175, a guard clamping ring 110, an insulator 120 and a ground shield 140. Collector 170 can require a rigid mechanical connection to the apparatus making up the ion mobility spectrometer 100, and yet can be electrically well insulated at the same time. This can be accomplished by using the insulator 120 with very high resistivity such as alumina, Macor, etc. During a polarity switchover, the electric potential across the insulator 120 reverses and insulator 120 can require time to re-polarize. A polarization current can be associated with the change in polarity across the insulator. The time period associated with the polarization current can be lengthened due to the phenomenon of dielectric absorption.

The insulators (including the insulator 120) are dielectrics and can exhibit some degree of dielectric absorption. The dielectric absorption relaxation time can be of the order of up to several milliseconds, which can contribute to a current that is detected at the collector 170. Electric field lines 130 are depicted in FIG. 1 across the insulator 120 between the guard clamping ring 110 and the collector 170. The collector 170 can remain at 0 volts, where the guard grid 175 can switch from about 90 volts (during a positive ion mode) to −90 volts (during a negative ion mode).

Figure 7:
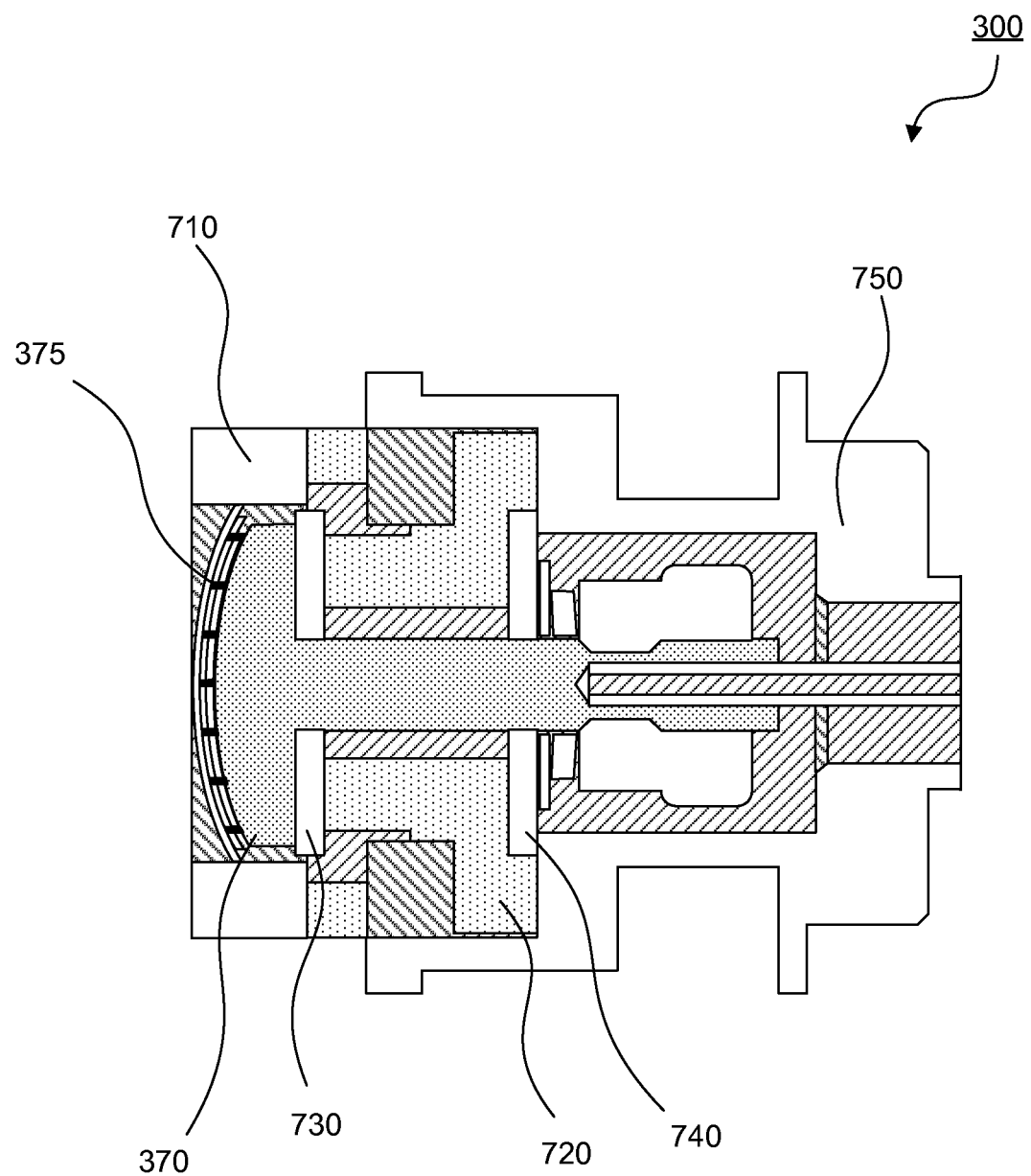
FIG. 7 is a cross sectional view of a guard grid and a collector portion of an ion mobility spectrometer consistent with an embodiment.

FIG. 7 depicts portion of a cross section of the ion mobility spectrometer 300 consistent with another embodiment. The portion of the ion mobility spectrometer 300 depicted in FIG. 7 includes the collector 370, the guard grid 375, a guard clamping ring 710, an insulator 730, an insulator 740, a grounded mount 720, and a ground shield 750. Although a ground shield and grounded mount 720 are discussed herein, a variety of grounding structures may be used to prevent and/or minimize electrical current from polarizing one or more of the insulators, e.g., insulators 740 and/or 730. For example, the a system implementing a grounding structure is capable of switching between positive and negative modes faster than a system which does not implement a grounding structure on a side of an insulator opposite a portion of the collector configured to collect ions. This may minimize the delay associated with the occurrence of dielectric absorption in the insulator(s), e.g., the dielectric absorption relaxation time of the insulator. In the embodiment depicted in FIG. 7, the insulator 730 and the insulator 740 can comprise ceramic material. In FIG. 7, the grounded mount 720 can be on the opposite side of the insulator 730 and the insulator 740 from the collector 370. In an embodiment, the insulator 120 from FIG. 1 has been replaced with two washers (the insulator 730 and the insulator 740). There can also be an insulator between the grounded mount 720 and the guard clamping ring 710. This insulating material can be a thin film such as, for example, KAPTON, a polyimide film developed by DuPont. Thus, in an embodiment, there is no direct insulation (other than air) between the guard grid 375, the guard clamping ring 710 and the collector 370, which can reduce the effect that dielectric absorption can have on contributing to a current detected at the collector 370 during polarity switchover.

In addition, the drift region 365 can be a source of current with an output current of around 10-100 pA. Accordingly, there can be a parasitic capacitance between the collector 370 and the guard grid 375 of approximately 1 pF where the voltage between these two components can be about 90 Volts. This can result in an accumulated charge on the collector 370 (and the guard grid 375) of about 100 pC.

During a rapid polarity switch, the accumulated charge can reverse sign, such that during rapid polarity switching involving many polarity switches, the accumulated charge can be reversed many times, where the peak current (i.e., (the change in charge)/(the change in time)) can be approximately ~100 pC/1 milliseconds ~100 nA, which can be 1,000 times larger than the typical output current from drift region 365. After a polarity switch, the voltages can stabilize in approximately 1-2 milliseconds consistent with an embodiment.

Figure 2:
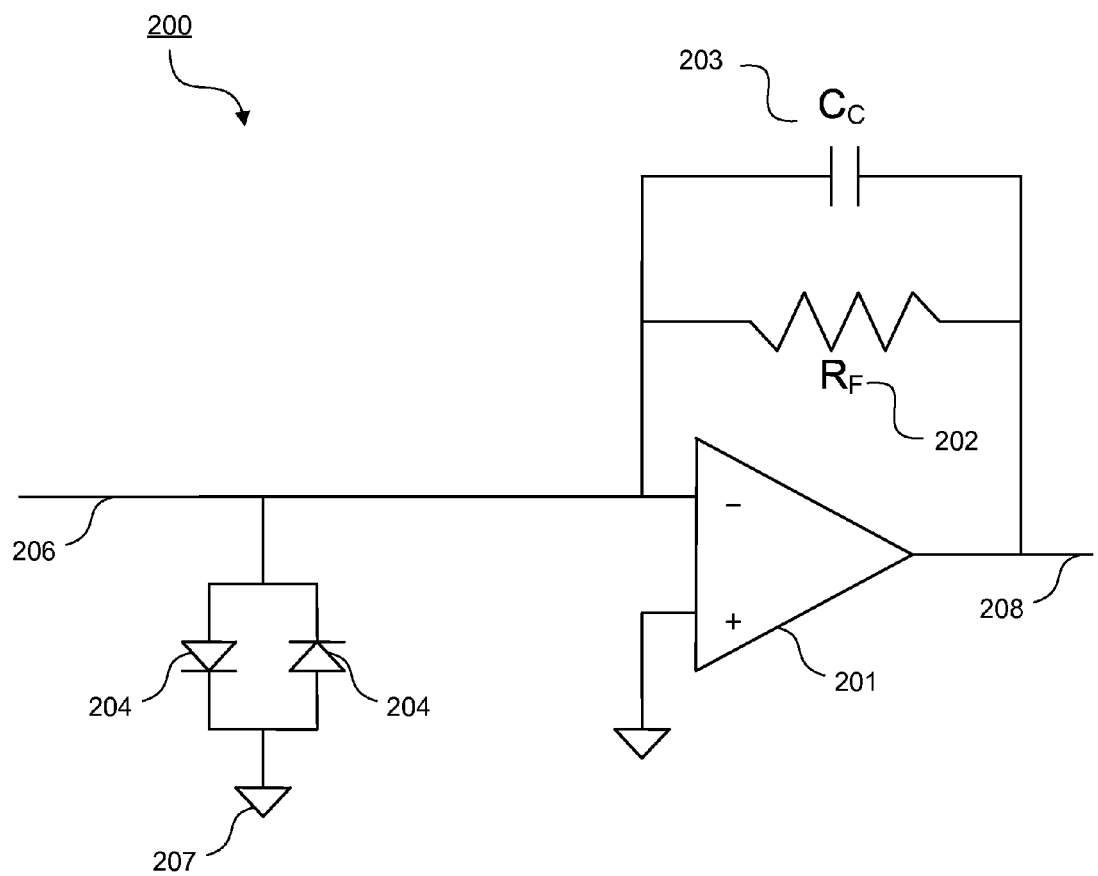
FIG. 2 is a circuit diagram of a portion of a two-stage preamplifier associated with an ion mobility spectrometer.

A preamplifier associated with an ion mobility spectrometer (a portion of which is depicted in FIG. 2) can be a transimpedance amplifier that uses a high input impedance operational amplifier along with relatively large feedback impedance (~GΩ) and can be incapable of handling input currents much greater than a few hundred pA. To allow for the preamplifier associated with FIG. 2 to handle 100 nA currents associated with polarity switchovers, a parallel circuit can be implemented as indicated.

Where such a parallel circuit includes diodes connected between the input and the ground that limit the input voltage to safe value (i.e., diodes 204 and 205 of FIG. 2), there can remain some charge stored on the diode capacitance (and other parasitic capacitances) following a switching current that can take a relatively long time to relax and cause a distortion in the baseline of the output signal (i.e., a distortion in the plasmagram).

In FIG. 2, circuit 200 comprises an inverting transimpedance amplifier 201 (current-to-voltage) whose gain is set by the value of a feedback resistor $R_F$ 202. Typical values of the feedback resistor $R_F$ 202 can range from 100 MΩ up to 10 s GΩ. A capacitor $C_C$ 203 (usually on the order of pF) can be required to ensure the stability of the feedback loop but it can also limit the frequency response of the circuit.

Some input current protection can be provided by a first diode 204 and a second diode 205 connected in opposite directions between an input 206 and ground 207. When the input node is kept at virtual ground (~0 Volts), there is virtually no current flowing through the diodes 204 and 205. During a current spike, the input voltage can be clamped at approximately 0.6 V. When the current spike is over, the circuit 200 can first discharge all input capacitances (approximately 20 to 30 pF) via the feedback resistor $R_F$ 202, which can take several hundreds of milliseconds. Afterwards, an output 208 can exponentially drop with the time constant set by the product of feedback resistor $R_F$ 202 and capacitor $C_C$ 203 and it can take seconds before a stable baseline is achieved.

Figure 8:
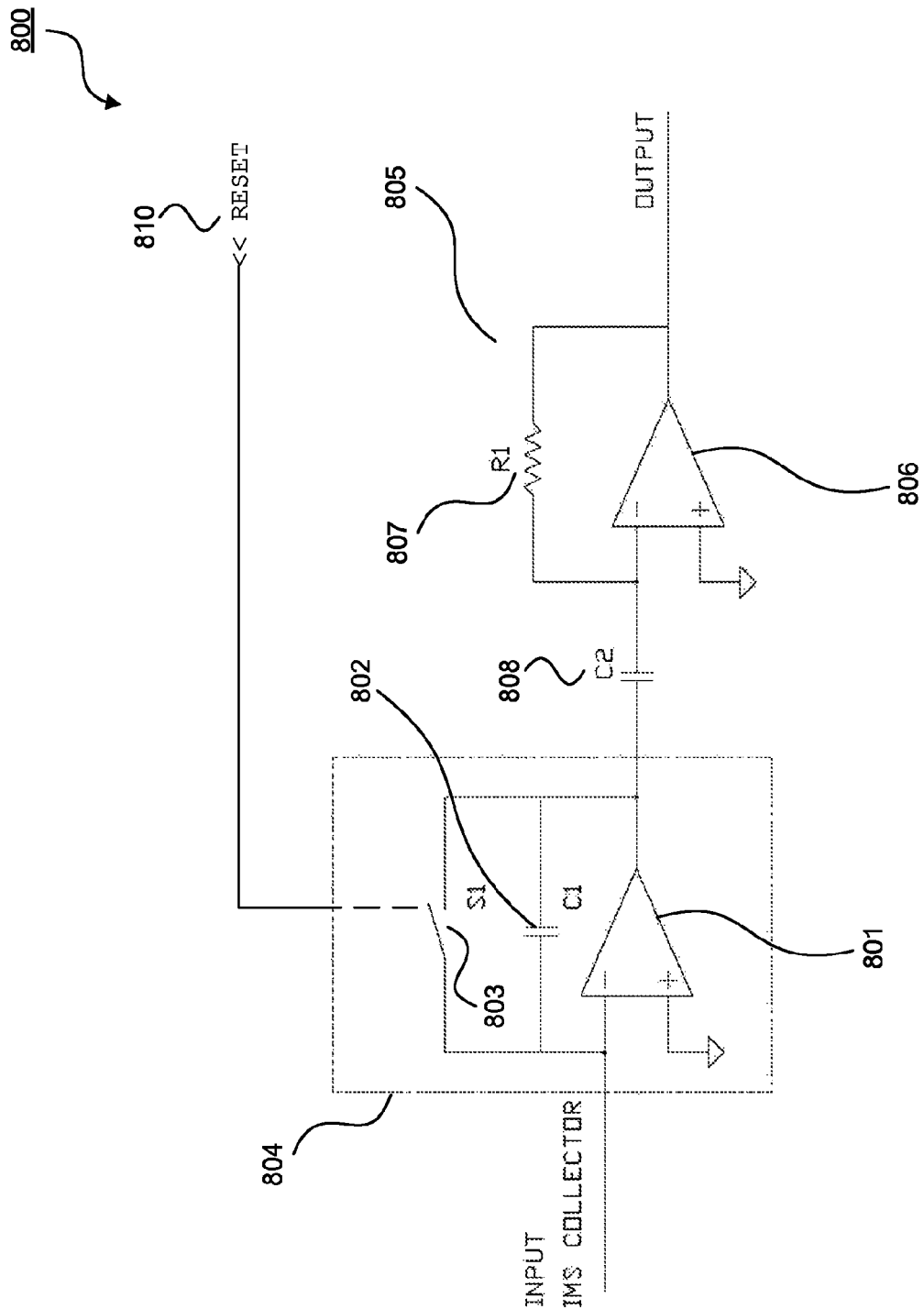
FIG. 8 is a schematic of a circuit diagram consistent with an embodiment.

FIG. 8 shows an embodiment of the preamplifier. Circuit 800 includes a first stage 820 (i.e., a transimpedance integrator circuit), which can include a first operational amplifier 801, a feedback capacitor C1 802 and a switch S1 803. The feedback capacitor C1 802 can be, for example, 2 pF. In an embodiment, the first operational amplifier 801, the feedback capacitor C1 802 and the switch S1 803 can be available as a single integrated circuit 804. The integrated circuit (IC) 804 can be, for example, IVC102 manufactured by Texas Instruments. Where the IC 804 is IVC102 as described above, the manufacturer's specified input current (includes operational amplifier bias current and switch leakage) can be 0.1 pA. The charge injection can be as small as 0.2 pC. In a further embodiment, the leakage current can be much smaller than the magnitude of a signal acquired from the collector 370 (<1 pA). Because a semiconductor switch can inject a charge during opening and closing operation, the amount of charge injection associated with the low-leakage switch 803 in an embodiment consistent with the disclosure can be selected to be below 1 pC. A second stage 805 (i.e., a differentiator circuit) can be based around an operational amplifier 806 which can be, for example, a low noise, precision operational amplifier such as OP27 manufactured by Analog Devices and includes a resistor R1 807 and a capacitor C2 808. The resistor R1 807 can be, for example, 100 kΩ, and the capacitor C2 808 can be, for example, 22 nF. The total transimpedance (ratio of output voltage to input current) of the circuit 800 can be given by R1·C2/C1 and may be, for example, about 1 GΩ. Other values for the resistor R1 807, the capacitor C1 802, and the capacitor C2 808 can include, for example, about 300 kΩ for the resistor R1 807, about 10 pF for the capacitor C1 802, and 33 nF for the capacitor C2 808. Generally, the values for the resistor R1 807, the capacitor C1 802, and the capacitor C2 808 can depend upon the application (e.g., the desired gain).

The switch 803 can be closed just before the start of the polarity transition, and can remain closed during fast-polarity switchover before opening a few milliseconds later when all grid voltages (such as the grid guard 375 voltage) have stabilized. Generally, the time period between the closing and the subsequent opening of the switch 803 can be less than 5 ms. The timing of the switch 803 can be digitally controlled by the RESET logic signal 810, which can be generated by the processor 401. One aspect of the circuit 800 consistent with the present disclosure is that transients introduced by the circuit 800 can be small in magnitude, thereby avoiding contributions to distortions in the baseline of the output signal.

Figure 9:
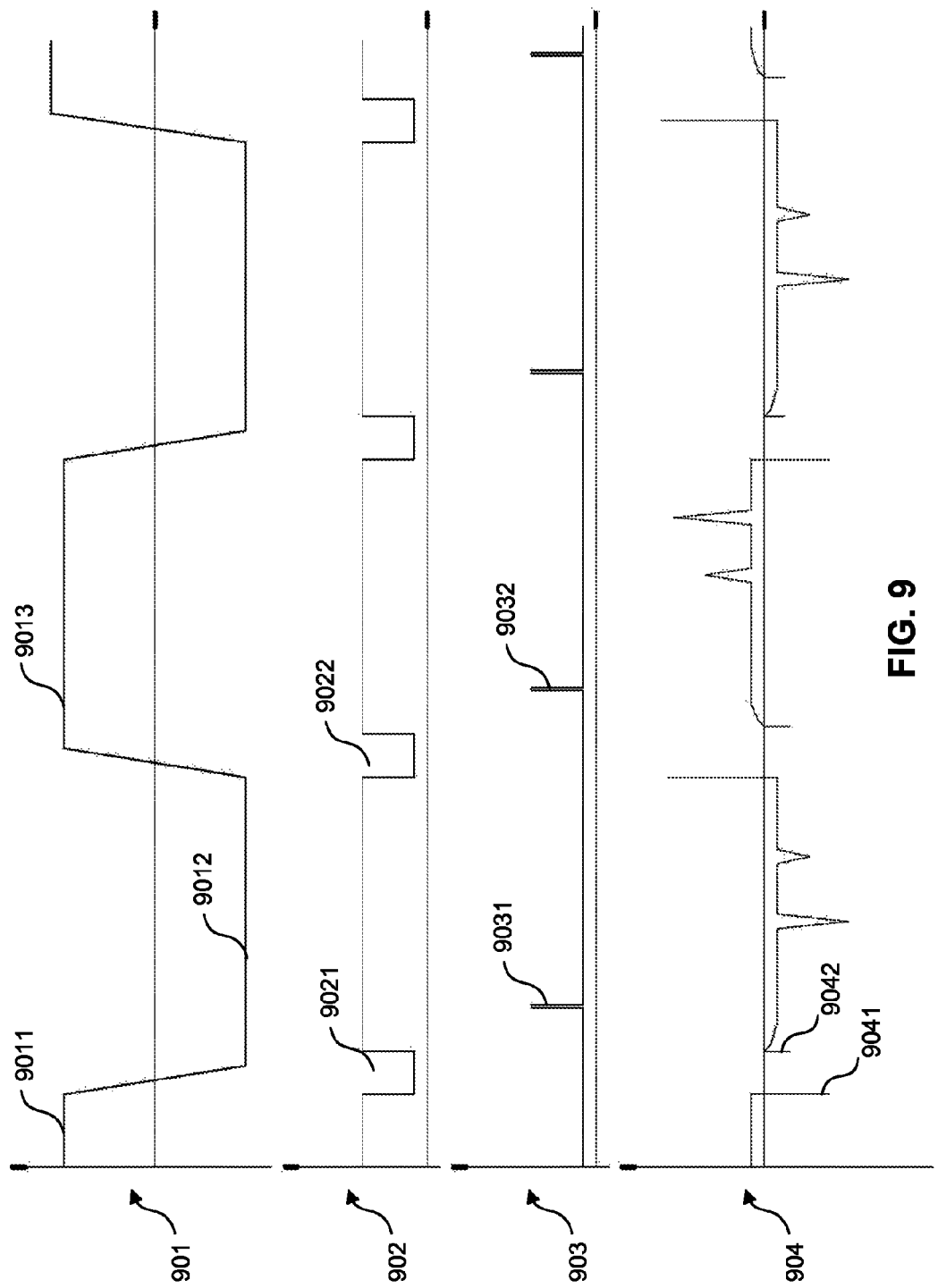
FIG. 9 depicts a timing trace of voltage switching consistent with an embodiment.

FIG. 9 shows timing of the signals. Trace 901 shows schematically the polarity of the ion mobility spectrometer 300 transitioning from positive ion mode 9011 to negative ion mode 9012 and back to positive ion mode 9013.

Trace 902 shows the timing of a RESET signal pulse 9021, associated with RESET logic signal 810 of switch 803, and which can be digitally controlled by the processor 401. This can be a logic signal active LOW. It can be asserted just before the start of the ion mobility spectrometer 300 polarity transition from positive ion mode 9011 to negative ion mode 9012 and can end after all the ion mobility spectrometer 300 voltages have stabilized. Another RESET signal pulse 9022 can be asserted just before the start of the ion mobility spectrometer 300 polarity transition from negative ion mode 9012 to positive ion mode 9013. The RESET signal pulses 9021 and 9022 can last about 2 milliseconds.

Trace 903 depicts a GATING pulse signal 9031 that can mark the beginning of the plasmagram data collection in negative ion mode 9012, and depicts a GATING pulse signal 9032 that can mark the beginning of the plasmagram data collection in positive ion mode 9013 (that is, GATING pulse signal 9032 can mark the beginning of the collection of data associated with a scan). The GATING pulses 9031 and 9032 can be configured to occur about 10 milliseconds after the ion mobility spectrometer 300 voltages have stabilized in either negative ion mode 9012 or positive ion mode 9013. This can allow for the ions within the drift region 365 of the ion mobility spectrometer 300 to establish a new equilibrium corresponding to the polarity thereby stabilizing the baseline current of the collector 370 of the ion mobility spectrometer 300.

Trace 904 is a preamplifier output. When the RESET signal pulse 9021 is asserted, the trace 904 can show a spike 9041 due to the discharging of capacitor C1 802. Then, for the duration of the RESET signal pulse 9021, the output can be essentially 0 volts. At the end of the RESET signal pulse 9021, there can be a small spike 9042 due to charge injection. Then there can be a period of a few milliseconds when the ion mobility spectrometer 300 baseline current stabilizes.

Plasmagram data can be collected in scans lasting 20 to 25 milliseconds following the GATING signal pulse 9031. Depending on the implementation, the ion mobility spectrometer 300 can be operated so as to change polarity after a scan (such as oscillating between positive ion mode 9011 and negative ion mode 9012 as shown in trace 901), or can collect several scans in one polarity before switching to the other polarity. For example, a switch of the polarity of the ion mobility spectrometer 300 can occur at any number of scans (i.e., every scan, every 5 scans, every 10 scans, or more).

When the ion mobility spectrometer 300 polarity is switched every several scans, the RESET pulse signal 9021 may be asserted after each scan and released before each GATING pulse signal 9031 or every several scans as long as the IC 804 does not saturate.

FIGS. 10 and 11 depict another embodiment of the preamplifier of FIG. 8 with a switch. FIG. 10 depicts a circuit 1000 which can be used in place of IC 804 of FIG. 8. Two states of the circuit 1000 are shown; the 'SWITCH OPEN' state depicted in FIG. 10 and the 'SWITCH CLOSED' state depicted in FIG. 11. The 'SWITCH OPEN' state depicted in FIG. 10 corresponds to the open setting of switch 803 and the 'SWITCH CLOSED' state depicted in FIG. 11 corresponds to the closed setting of switch 803—and which is connected to the RESET operation discussed above.

A diode D1 1001 and a diode D2 1002 can be connected between an input node 1003 and two switches, S1 1004 and S2 1005. During operation in positive ion mode or negative ion mode, the diodes 1001 and 1002 can be switched to ground 1006 and 1014. The input node 1003 can be held at virtual ground by a feedback capacitor C 1007 across an amplifier 1008. The equivalent series resistance of the diodes 1001 and 1002 at 0 V bias can be very high; close to TΩs therefore, there can be virtually no current flowing through those diodes 1001 and 1002 even if there is small offset voltage (typically ~1 mV) present on the input node 1003.

During RESET, (i.e., during polarity switchover), both switches, S1 1004 and S2 1005 can be flipped, as illustrated in FIG. 11 thus connecting all four diodes 1001, 1002, 1009 and 1010 into a bridge configuration with all four diodes 1001, 1002, 1009 and 1010 forward biased. The bridge can act as a feedback resistor whose resistance equals to the equivalent series resistance of the diodes 1001, 1002, 1009 and 1010. The bias current used can be about 8 μA, the equivalent series resistance can be of the order of ~6 kΩ, which can be much less than the operating impedance of the circuit 1000 in the 'SWITCH OPEN' state as illustrated in FIG. 10. This keeps an output voltage 1013 close to 0 V even if input current reach 100 s of μA.

When the RESET signal terminates, the diodes D1 1001 and D2 1002 can be connected back to the ground 1006 and 1014, as depicted in FIG. 10. There can be a small charge on each diode 1001 and 1002 equal to forward voltage times diode capacitance. However, the two diodes 1001 and 1002 can have opposite charges, and when they are discharged, only the difference caused by mismatch of the charges becomes injected into the input 1003 of the circuit 1000. The total charge injected can be under 1 pA The amplifier 1008 can be, for example, a dual JFET (junction gate field-effect transistor), such as SST441 manufactured by Vishay Siliconix, driving a high precision low noise operational amplifier such as OPA2227 manufactured by Texas Instruments. Resistors R1 1011 and R2 1012 can be 1 MΩ each (i.e., they can be matched), diodes D3 1009 and D4 1010 can be a dual diode such as MMBD3004S manufactured by Diodes Incorporated, and the switches S1 1004 and S2 1005 can be implemented using a low capacitance, low charge injection dual SPDT switch such as ADG1236 manufactured by Analog Devices.

Diodes D1 1001 and D2 1002 can be selected to have low capacitance and the largest possible equivalent series resistance. The design can use p-n junction JFET devices including, for example, SST-J212 manufactured by Vishal Siliconix.

Where data associated with a plasmagram is acquired during fast-switching operation, systems and methods consistent with yet another embodiment of the present disclosure can take into account a non-linearity that can be introduced into plasmagrams as a result of a fast-switching operation. Specifically, it is found that fast-switching can introduce a background distortion into the scan data that is processed to generate a plasmagram. An exemplary effect of this distortion is illustrated in the plasmagram 1200 depicted in FIG. 12. Specially, the region 1201 and the region 1202 exhibit a baseline curve that is not even with the ordinate. A compensation for the non-linearity of this distortion can be accomplished by subtracting a value from a fitted curve from each value of the plasmagram in real-time before the plasmagram data (such as the segment data or the scan data) is analyzed by the processor 401 or displayed. This can reduce the effect of the plasmagram non-linearity and allow the plasmagram background to approach the zero-level of the ordinate (i.e., it can normalize the measured values in the time domain).

Steps associated with normalizing plasmagram data can generally be divided into two parts and is illustrated in FIG. 13. In the first part, an offline calculation 1306 can be performed on a collection 1302 of segment data associated with fast-polarity switching to develop, among other things, fitting coefficients (step 1328). In the second part 1308, these fitting coefficients can be used to subtract a portion of the amplitude from each scan data value acquired by the collector 370 in real-time (i.e., as the scan data is collected, or prior to the analysis or display of the resulting segment data by the processor 401).

Figure 12:
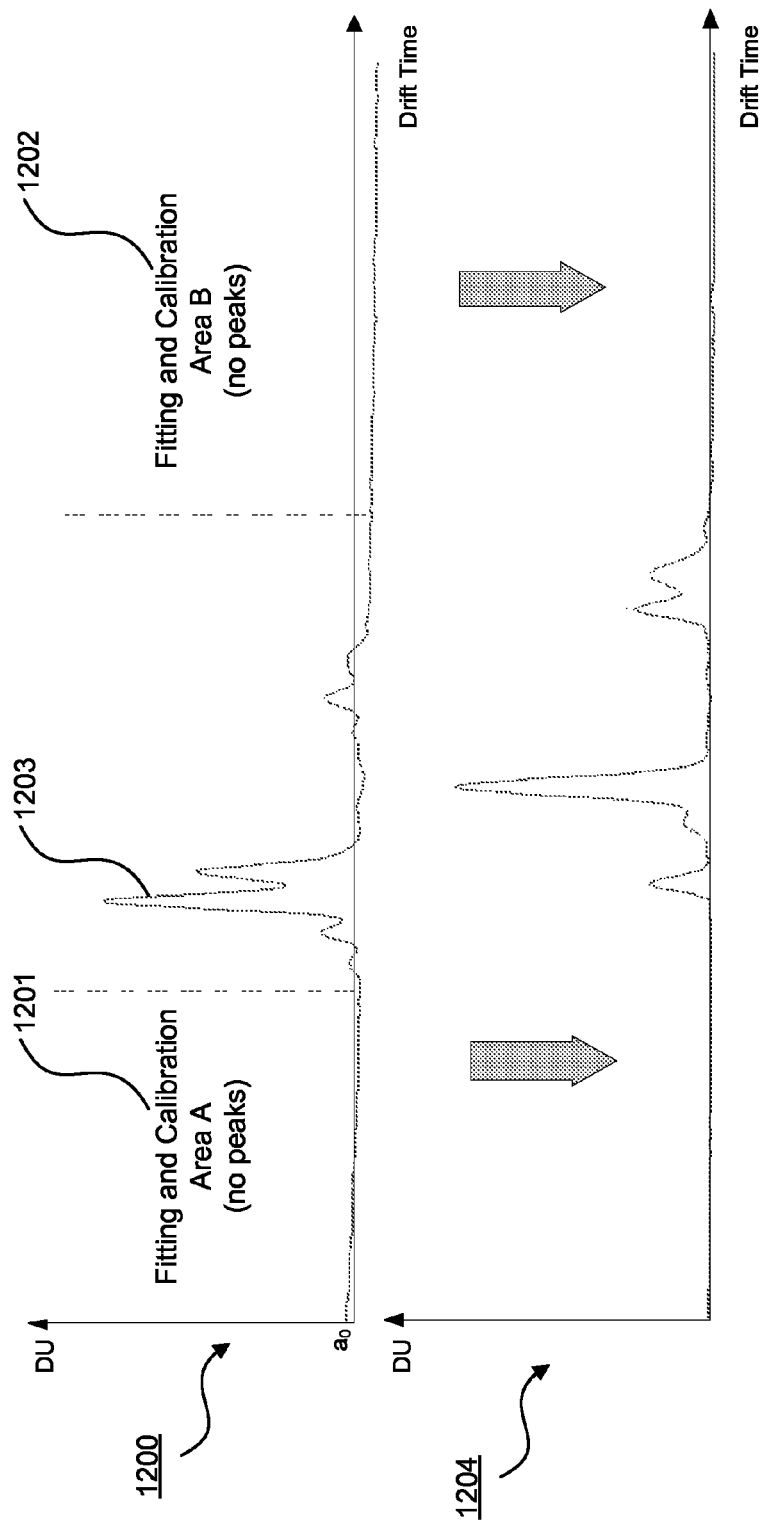
FIG. 12 depicts a plasmagram before and after it has been normalized.

The offline curve fitting calculation 1306 can include several steps. First, a sufficient number of clean plasmagrams (i.e., collections 1302 of segment data) can be collected such that a processor (which can be either processor 401, or another processor), under control of software instructions or otherwise, can perform a least-squares fitting of a fitting and calibration area of the plasmagram to a polynomial form (step 1320) or to an exponential form (step 1316). The regions of the plasmagram curves that are fitted—referred to as fitting and calibration areas—are illustrated in FIG. 12. Specifically, plasmagram 1200 includes Fitting and Calibration Area A (no peaks) 1201 and Fitting and Calibration Area B (no peaks) 1202. Fitting and Calibration Areas A 1201 and B 1202 can be selected or identified (step 1314) by the lack of significant peaks. Preferably, Fitting and Calibration Areas A 1201 and B 1202 can be selected to exhibit as little noise as possible. The segment data 1312 that can be used for the offline calculation 1306 can be collected—for example—from blank test samples, and when no chemicals have been introduced to the ion mobility spectrometer 300.

As indicated in FIG. 12, plasmagrams used for purposes of offline calculation 1306 can have relatively large fitting areas 1201 and 1202. The processor can perform a least squares fit of the selected fitting area to an exponential form $f_{exp}(t) = ae^{-bt}$ (step 1316) and define a fitting error (step 1318). The processor can also perform a least squares fit of the selected fitting area to polynomial form $$f_{poly}(t) = a_0 + a_1 t + a_2 t^2 + a_3 t^3 + \ldots + a_N t^N = \sum_{k=0}^{N} a_k t^k$$

(step 1320) and define a fitting error (step 1322). The region associated with the selected fitting areas can be fitted to either a polynomial or an exponential function, whichever gives better approximation (step 1324) (i.e., whichever approximation yields a smaller fitting error). The fitting error associated with step 1318 is the difference between the least squares fit to the exponential form $f_{exp}(t) = ae^{-bt}$ (step 1316) and the plasmagram data. The fitting error associated with step 1322 is the difference between the least squares fit to the polynomial form $$f_{poly}(t) = a_0 + a_1 t + a_2 t^2 + a_3 t^3 + \ldots + a_N t^N = \sum_{k=0}^{N} a_k t^k$$

(step 1320) and the plasmagram data.

Based upon which approximation yields a smaller fitting error (step 1324), the processor can determine whether to use the fitting to the exponential curve (step 1316) or the fitting to the polynomial curve (step 1320). This can be based on the value of fitting error, which can itself depend on the level of plasmagram noise. The processor can then identify a fitting form and average fitting coefficients (step 1328), which can be the result of many plasmagrams and instruments. The processor can also identify the standard deviation of fitting errors between collected plasmagrams (step 1326). The standard deviation can include the change in error associated with the same ion mobility spectrometer 300 and/or the change in error between different ion mobility spectrometers 300.

The calculation 1308 associated with the second part can be stored as software instructions in storage 402 and can be available to processor 401 as scan data and/or segment data is made available through collector interface 403. The processor 401 can be configured to collect all of the acquired data into a set $\{r_n(t)\}$ (step 1330). For each element $r_n(t)$ of the plasmagram set $\{r_n(t)\}$, the processor 401 can be configured to calculate the corresponding value of the fitted curve determined in step 1328 (F(t)) and any associated error (step 1326). It is possible to use a nested polynomial for faster calculation of F(t). The processor 401 can be configured to subtract this background contribution F(t) from each element of the plasmagram set $\{r_n(t)\}$ (step 1334). After such subtraction, the non-linear distortion, such as exhibited in the plasmagram 1200, can be eliminated. The end result can be plasmagram data (step 1310) with a flat baseline. Plasmagram 1204 in FIG. 12 depicts a curve similar to plasmagram 1200, but with the background distortion substantially eliminated.

Other embodiments of the invention will be apparent to those skilled in the art from consideration of the specification and practice of the embodiment disclosed herein. Although one or more methods have been described in conjunction with the ion mobility spectrometer 300, it is to be apparent that the method may be used with other devices and configurations of ion mobility spectrometers. Although some embodiments are described as being under computer control (e.g., a computer configured to execute a program of instructions), it is to be apparent that some of these functions may be carried out using hardware and/or software such as an application specific integrated circuit (ASIC) configured to perform a specific task, e.g., managing polarity switching, etc. It is intended that the specification and examples be considered as exemplary only, with a true scope and spirit of the invention being indicated by the following claims.

We claim:

1. A detector for an ion mobility spectrometer comprising:
   a collector configured to collect ions from a sample;
   an electrical insulator for mounting the collector in a housing that at least partially defines a drift region of an ion mobility spectrometer;
   wherein a portion of the collector configured to collect the ions is supported by the electrical insulator, and the electrical insulator is separated from other conductive or polarizable structures of the IMS cell by a grounded structure.

2. The detector of claim 1, wherein the detector further comprises another electrical insulator configured to be disposed at least partially between the grounded structure and the housing.

3. The detector of claim 2, wherein the detector further comprises another grounded structure disposed between the other electrical insulator and the housing.

4. The detector of claim 1, wherein the grounded structure comprises a ground shield.

5. The detector of claim 1, wherein the grounded structure comprises a grounded mount.

6. The detector of claim 1, wherein the grounded structure is substantially at zero volts.

7. The detector of claim 1, wherein the electrical insulator is in direct contact with the collector and the grounded structure.

\* \* \* \* \*